United States Patent [19]

Mori

[11] Patent Number: 4,785,811

[45] Date of Patent: Nov. 22, 1988

[54] SOLAR RAY ENERGY RADIATION DEVICE FOR USE IN MEDICAL TREATMENT

[76] Inventor: Kei Mori, 3-16-3-501, Kaminoge, Setagaya-ku, Tokyo, Japan

[21] Appl. No.: 21,086

[22] Filed: Mar. 3, 1987

[30] Foreign Application Priority Data

May 13, 1986 [JP] Japan .................. 61-109232

[51] Int. Cl.[4] .................. A61N 3/00; F21V 7/00; F21V 7/04; H05B 37/02
[52] U.S. Cl. .................. 128/397; 128/372; 362/1; 362/32; 362/285; 315/149
[58] Field of Search .............. 128/362, 372, 395, 396, 128/397; 250/205, 227; 315/149, 150, 157, 308; 362/32, 1

[56] References Cited

U.S. PATENT DOCUMENTS

| 668,404 | 2/1901 | Hanneborg | 128/372 |
| 4,279,254 | 7/1981 | Boschetti et al. | 128/395 |
| 4,358,717 | 11/1982 | Elliot | 315/308 |
| 4,690,141 | 9/1987 | Castel et al. | 128/397 |
| 4,695,769 | 9/1987 | Schwelckardt | 315/149 |

FOREIGN PATENT DOCUMENTS

| 2550327 | 5/1977 | Fed. Rep. of Germany | 128/395 |
| 3528282 | 2/1986 | Fed. Rep. of Germany | 128/395 |
| 2445153 | 8/1980 | France | 128/397 |
| 139210 | 12/1979 | German Democratic Rep. | 128/395 |

Primary Examiner—Richard C. Pinkham
Assistant Examiner—Mark S. Graham
Attorney, Agent, or Firm—Jordan and Hamburg

[57] ABSTRACT

A solar ray energy radiation device for use in medical treatment which comprises one or more optical conductor cables through which solar ray energy is transmitted. A light projector is installed at the end portion of the optical conductor cables, along with a control box for controlling the position of the light projector and a light sensor which is disposed in the light projector. The light sensor detects the solar ray energy emitted from the optical conductor cable, and the distance between the light projector and an object to be radiated is controlled on the basis of the detection value obtained by the light sensor.

9 Claims, 3 Drawing Sheets

SOLAR RAY ENERGY RADIATION DEVICE FOR USE IN MEDICAL TREATMENT

BACKGROUND OF THE INVENTION

The present invention relates to a solar ray energy radiation device for use in medical treatment, in particular, a solar ray radiation device for use in medical treatment which radiates light rays energy corresponding to the visible light ray compoents of solar rays onto the diseased part or the desired portion of a patient in order to perform various medical treatments, or radiates the same onto the surface of a person's skin for administering a beauty treatment or for the promotion of heath.

In recent years, a large number of persons suffer from incurable diseases such as arthritis, neuralgia and rheumatism, or pain from an injury, a bone fracture, or from an ill-defined disease. Furthermore, any person cannot avoid having their skin show signs of aging which happens gradually from a comparatively young age. On the other hand, the present applicant has previously proposed focusing solar rays or artificial light rays, by use of lenses or the like, to guide the same into an optical conductor, and to transmit the same solar rays or artificial light rays onto an optional desired place through the optical conductor. Those light rays transmitted in such a way are employed for use in illuminating or for other like purposes, as for example, to cultivate plants, chlorella, or the like. In the process, visible light rays not containing ultraviolet, infrared and other harmful rays promote the body's health and prevent the person's skin from the appearance of aging. Furthermore, those visible light rays appear to have noticeable beneficial effects in helping persons to recover from arthritis, neuralgia, bedsores, rheumatism, injuries, bone fractures, or the like, and of alleviating the pain from those diseases. Such effects have been witnessed by the present applicant.

On the basis of the afore-mentioned discovery, the present applicant has proposed various light ray radiation devices for use in medical treatment capable of radiating light rays corresponding to the visible light ray components of solar rays containing therein no harmful ultraviolet rays, infrared rays, or other harmful rays.

A solar ray radiation device for use in medical treatment which has been previously proposed by the present applicant has an optical conductor cable and a light projector. Solar rays or artificial light rays are guided into the optical conductor cable from the end portion thereof and transmitted therethrough. The light rays (the white-colored light rays) corresponding to the visible light ray components of the solar rays are transmitted through the optical conductor cable in such a manner as previously proposed in various ways by the present applicant. A light projector is installed at the light ray emitting end portion side of the above-mentioned optical conductor cable.

At the time of administering medical treatment, a patient is laid on the medical treatment chair and light rays consisting of the visible light ray components are transmitted through the optical conductor cable and radiated onto the diseased part of the patient as mentioned before. The light rays to be radiated onto the diseased part of the patient are the ones to be radiated to the visible light ray components of solar rays not containing ultraviolet rays, infrared rays, and other harmful rays, as mentioned above. Thereby, it is possible to perform medical treatment without the patient suffering from any harmful effects caused by those harmful rays.

However, when utlilizing the solar rays in practice, the visible light ray components change depending on the weather and time of day. Therefore, even though the solar ray radiator is set at a location for obtaining a most suitable amount of light rays to be radiated, the amount of light rays changes during treatment. Consequently, it follows that the intensity of the light rays is decreased too much to administer an effective medical treatment. There also exists a danger of the patient getting burned when the intensity turns out to be too strong.

SUMMARY OF THE INVENTION

It is an object of the present invention to provide a solar ray energy radiation device capable of radiating a suitable amount of light rays onto the object to be radiated.

It is another object of the present invention to provide a solar ray energy radiation device capable of radiating a constant amount of solar rays which is predetermined, onto the object to be radiated.

It is another object of the present invention to provide a solar ray energy radiation device capable of keeping the intensity of the solar rays being focused onto the object at a predetermined level.

It is another object of the present invention to provide a solar ray radiation device for use in medical application in the treatment of various medical problems for administering beauty treatments and for promoting health.

It is another object of the present invention to provide a solar ray radiation device for effectively emitting solar rays corresponding to the visible solar ray components of solar rays that do not contain harmful rays such as ultraviolet or infrared.

It is another object of the present invention to provide a solar ray energy radiation device that is safe to use.

The above-mentioned features and other advantages of the present invention will be apparent from the following detailed description which goes with the accompanying drawings.

DESCRIPTION OF THE PREFERRED EMBODIMENTS

Figure 1:
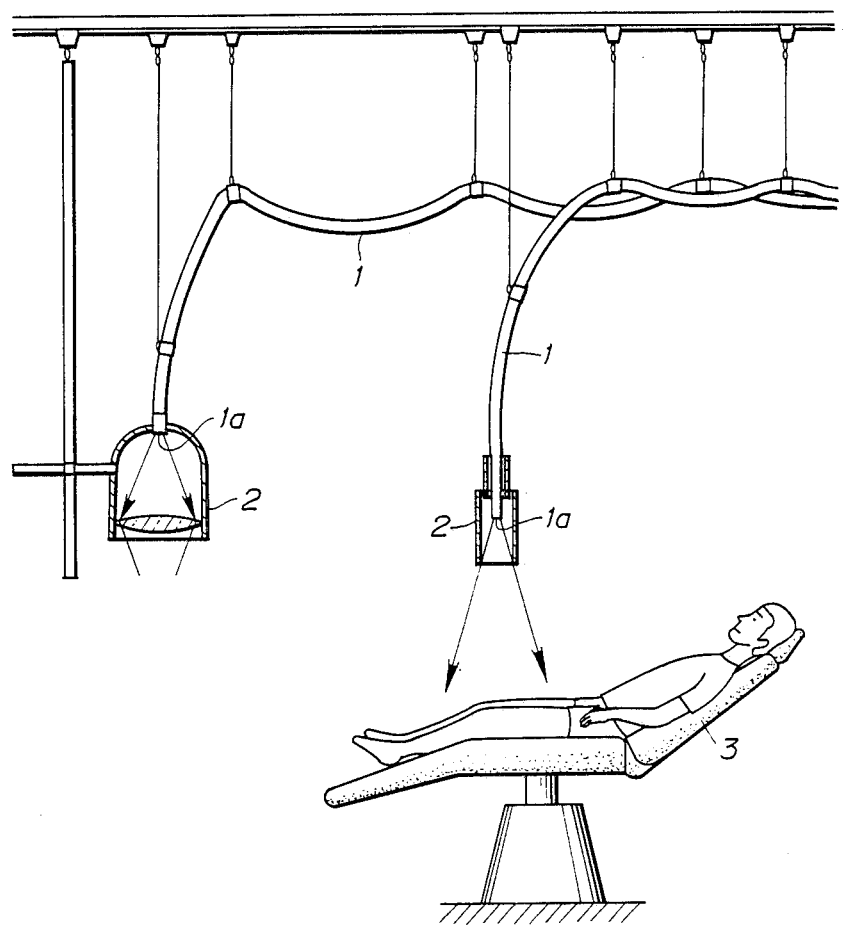
FIG. 1 is a construction view for explaining an embodiment of a solar ray radiation device for use in medical treatment previously proposed by the present applicant.

FIG. 1 is a construction view for explaining an embodiment of a solar ray radiation device for use in medical treatment previously proposed by the present applicant. In FIG. 1, 1 is an optical conductor cable. Solar rays or artificial light rays are guided into the optical conductor cable 1 from the end portion thereof (not shown) and transmitted therethrough. The light rays (the white-colored light rays) corresponding to the visible light ray components of the solar rays are transmitted through the optical conductor cable 1 in such a manner as previously proposed by the present applicant. In the same Figure, 2 is a light projector installed at the light ray emitting end portion 1a of the above-mentioned optical conductor cable 1, and 3 is a medical treatment chair.

At the time of administering medical treatment, a patient is laid on the medical treatment chair 3 and light rays consisting of the visible light ray components transmitted through the optical conductor cable 1 are radiated onto the diseased part of the patient as mentioned before. The light rays to be radiated onto the diseased part of the patient are the ones corresponding to the visible light ray components of solar rays and not containing ultraviolet, infrared, or other harmful rays, as mentioned above. Therefore, it is possible to administer medical treatment without any harmful side-effects caused by ultraviolet rays, infrared rays, or other harmful rays.

However, in actual practice, the visible light ray components change depending on the weather and time of day. Therefore, even though the solar ray radiator is set at a proper location for obtaining the most suitable amount of light rays to be radiated, the amount of light rays changes during a given time. Consequently, it may follow that the intensity of the light rays is decreased and it is impossible to administer an adequate amount of solar energy for medical treatment. There also exists a danger of burning the object to be radiated in case the intensity of the light rays is increased.

Figure 2:
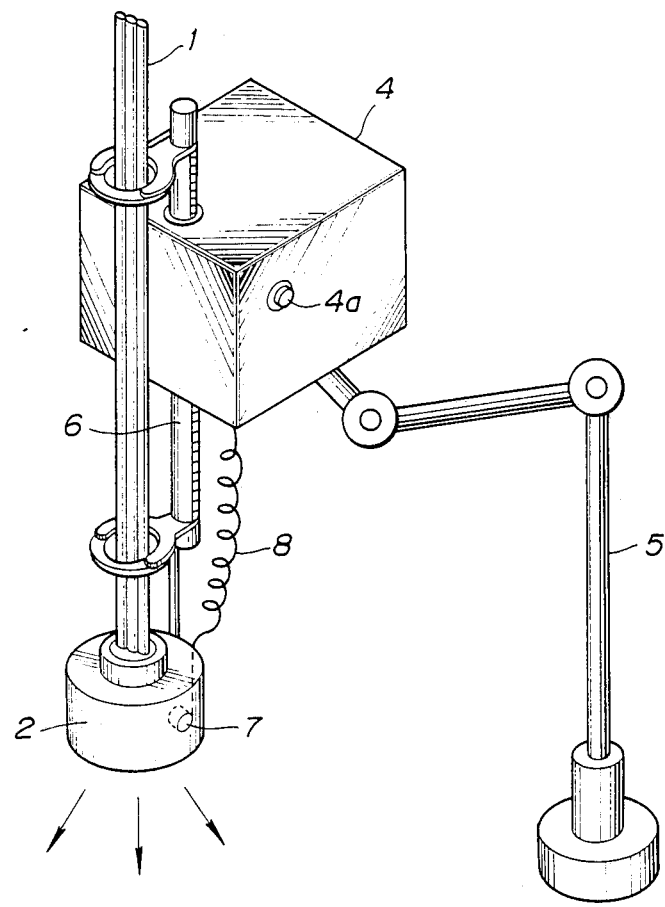
FIG. 2 is a construction view for explaining an embodiment of a solar ray energy radiation device for use in medical treatment according to the present invention.

FIG. 2 is a construction view for explaining an embodiment of a solar ray energy radiation device for use in medical treatment according to the present invention. In FIG. 2, 4 is a control box, 5 is a stand for supporting the control box 4, 6 is a rack bar, 7 is a light sensor, and 8 is a lead wire. Furthermore, the same reference numerals are attached to the parts performing the same action as that of the parts of the conventional device shown in FIG. 1. Furthermore, the control box 4 contains therein a gear for moving the rack bar 6 up and down in combination therewith, a motor for rotatably driving the gear, a micro-computer for controlling the motor in accordance with a signal detected by the light sensor 7.

When the device according to the present invention, is used, a meter for measuring the amount of light rays such as a light intensity meter, or the like, is put on the surface of an object to be radiated, and the light projector 2 is caused to approach the object to a location keeping a predetermined distance therefrom and the rack bar 6 is set at approximately the central position of the control box 4. In such a manner, the light intensity meter indicates the light intensity value suitable for the object to be radiated. Next, turning a knob 4a sets the intensity of light, and the motor which drives the rack bar stops. Consequently, if the solar ray energy emitted from the optical conductor cable 1 does not change at all afterwards, the detection signal generated by the light sensor 7 also remains constant and therefore, the light projector 2 remains fixed in a predetermined position as mentioned above.

However, when the intensity of the light rays emitted from the optical conductor cable 1 decreases, for example, the detection signal generated by the light sensor 7 also decreases. Then, the motor in the control box 4 rotates so as to push the rack bar 6 downward. Thereby, the rack bar 6 is pushed down in proportion to the decrease in the detection signal generated by the light sensor 7. In such a manner, a constant amount of light ray energy is supplied to the object to be radiated.

On the other hand, when the intensity of the light rays emitted from the optical conductor cable 1 increases, the detection signal generated by the light sensor 7 also increases. Then, the motor rotates so as to push the rack bar 6 upward so as to move the light projector 2 away from the object to be radiated. However, in the case where the detection output signal of the light sensor 7 decreases to a predetermined set level or less, or in the case that the light projector approaches too closely to the object to be radiated, an ultrasonic sensor or a pressure sensor disposed on the light projector, used to measure the distance between the light projector and the object to be radiated, stop the downward movement of the light projector 2 in order to ensure the safety of the object to be radiated.

Consequently, according to the present invention, a desired constant amount of light ray energy can be radiated. Furthermore, there is no fear of getting burned under the influence of strong light ray energy radiation. And further, although an embodiment of the device having a control box 4 and supported by the stand 5 is shown in FIG. 2, it will be easily understood that the control box 4 may be suspended from a rail installed on the ceiling or the like.

Figure 3:
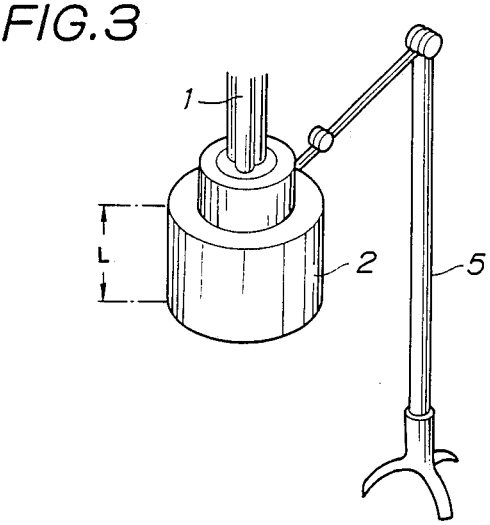
FIGS. 3 through 5 are, respectively, partial construction views for explaining other simplified embodiments of the same.

FIG. 3 is a partial construction view showing a simplified embodiment of the solar ray energy radiation device for use in medical treatment. In this embodiment, the light projector 2 can be moved up and down manually, and the length L of the light projector 2 is selected not to burn the subject to be radiated by the light ray energy emitted from the optical conductor cable 1.

Figure 4:
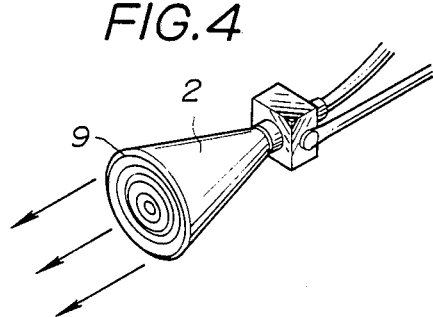
Figure 5:
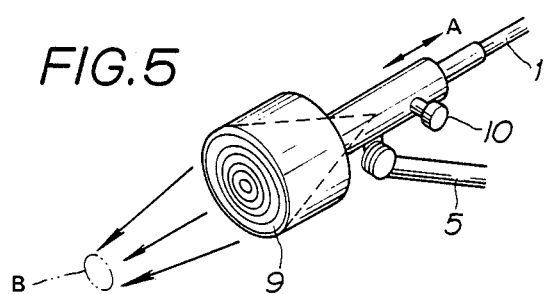

FIGS. 4 and 5 are, respectively, partial construction views showing other simplified embodiments. In the embodiment of FIG. 4, a Fresnel lens 9 is attached to the enlarged end portion of the light projector 2 in order to convert the light rays emitted from the optical conductor cable 1 to approximately parallel light rays. In the embodiment of FIG. 5, a convex Fresnel lens 9 is attached to the end portion of the light projector 2 and the position of the light projector 2 can be adjusted along the directions shown by an arrow A by loosing a bolt 10 in relation to the optical conductor cable 1. In this embodiment, the area of a radiated portion B can be changed to a more desirable one by adjusting the position of the light projector 2.

A Fresnel lens may also be employed in the embodiment of FIG. 2.

As is apparent from the foregoing description, according to the present invention, the amount of light ray energy radiated onto an object to be radiated turns out to be almost constant. Consequently, the efficiency of the medical treatment can be raised by radiating the almost constant light ray energy onto the object to be radiated, and there exists no danger of the subject getting burned even though the radiated light ray energy is increased considerably.

I claim:

1. A medical treatment device utilizing the visible light ray component of solar rays, comprising optical conductor means receiving and transmitting therethrough light rays corresponding to the visible light rays component of solar rays and excluding ultraviolet and infrared rays, said conductor means having a light-emitting end portion, a projector means on which said light-emitting end portion is mounted, a light-sensor means on said projector means for detecting the intensity of the rays emitted from said optical conductor means, actuating means operable to move said projector means towards and away from a person's body to be treated, and control means operably connected to said actuating means and to said light-sensor means for controlling the position of said projector means relative to said person's body depending on the value of the intensity of the solar rays detected by said light-sensor means.

2. A medical treatment device according to claim 1 wherein said optical conductor means has a longitudinal axis, said projector means being moved by said actuating means in a direction parallel to said longitudinal axis.

3. A medical treatment device according to claim 1 wherein said projector means comprises a projector structure and a lens means mounted in said projector structure spaced from said light-emitting end portion of said optical conductor means for focusing light rays emitted from said light-emitting end portion.

4. A medical treatment device according to claim 1 wherein said projector means comprises a projector structure and a Fresnel lens mounted on said projector structure for converting the light rays emitted from said optical conductor means to approximately parallel light rays.

5. A medical treatment device according to claim 1 wherein said projector means comprises a projector structure and a lens means mounted on said projector structure.

6. A medical treatment device according to claim 1 wherein said optical conductor means has a longitudinal end section extending from said light-emitting end portion, said actuating means being disposed about said longitudinal end section, said control means comprising a motor means for moving said actuating means in a direction parallel to the longitudinal axis of said longitudinal end section.

7. A medical treatment device according to claim 1 wherein said control means is operable to actuate said actuating means to move said projector means towards and away from said person's body in proportion to the change in the intensity of the light rays emitted from said optical conductor means and detected by said light-sensor means.

8. A medical treatment device according to claim 1 wherein said control means comprises a manually operable control knob for manually inputting a light-intensity setting corresponding to the light intensity detected by said light-sensor means at the beginning of use of the medical treatment device.

9. A medical treatment device according to claim 1 wherein said projector means comprises a projector structure having a generally cylindrical configuration with two ends, one of said ends being open and the other of said ends receiving said light emitting end portion of said optical conductor means.

* * * * *